(12) United States Patent
Lucas et al.

(10) Patent No.: US 8,236,954 B2
(45) Date of Patent: Aug. 7, 2012

(54) PROCESSES FOR PREPARING BENZIMIDAZOLE THIOPHENES

(75) Inventors: Amanda Caroline Lucas, Stevenage (GB); Robert M. Harris, Stevenage (GB); Christopher James Nichols, Stevenage (GB); Andrew Jonathan Whitehead, Stevenage (GB)

(73) Assignee: GlaxoSmithKline LLC, Philadelphia, PA (US)

( * ) Notice: Subject to any disclaimer, the term of this patent is extended or adjusted under 35 U.S.C. 154(b) by 363 days.

(21) Appl. No.: 12/665,041

(22) PCT Filed: Jun. 23, 2008

(86) PCT No.: PCT/US2008/067867
§ 371 (c)(1),
(2), (4) Date: Dec. 17, 2009

(87) PCT Pub. No.: WO2009/002916
PCT Pub. Date: Dec. 31, 2008

(65) Prior Publication Data
US 2010/0256376 A1    Oct. 7, 2010

Related U.S. Application Data

(60) Provisional application No. 60/946,209, filed on Jun. 26, 2007.

(51) Int. Cl.
*C07D 409/04* (2006.01)
(52) U.S. Cl. .................. 544/370; 514/254.06
(58) Field of Classification Search ................. None
See application file for complete search history.

(56) References Cited

U.S. PATENT DOCUMENTS

2009/0005398 A1* 1/2009 Dar .................. 514/254.06

FOREIGN PATENT DOCUMENTS

| WO | 2004014899 A | 2/2004 |
| WO | 2007030361 A | 3/2007 |

* cited by examiner

*Primary Examiner* — Emily Bernhardt
(74) *Attorney, Agent, or Firm* — Robert H. Brink

(57) ABSTRACT

A process for preparing benzimidazole thiophenes including 5-{6-[(4-methylpiperazin-1-yl)methyl]-1H-benzimidazol-1-yl}-3-{(1R)-1-[2-(trifluoromethyl)phenyl]ethoxy}thiophene-2-carboxamide.

4 Claims, No Drawings

PROCESSES FOR PREPARING BENZIMIDAZOLE THIOPHENES

CROSS-REFERENCE TO RELATED APPLICATIONS

This application is filed pursuant to 35 USC 371 as a United States National Phase Application of International Patent Application Serial No. PCT/US2008/067867 filed on Jun. 23, 2008, which claims priority from 60/946,209 filed on Jun. 26, 2007 in the United States.

BACKGROUND OF THE INVENTION

The present invention relates to a novel process for preparing benzimidazole thiophene compounds. Benzimidazole thiophene compounds which may be prepared using the processes of the present invention are described in PCT Publication Nos. WO2004/014899, WO2007/036061 and WO2007/030359, all to SmithKline Beecham Corp. Pharmaceutical formulations and therapeutic uses and other processes for the preparation of such compounds are also disclosed therein.

A regioselective synthesis of benzimidazole thiophene compounds is disclosed in PCT Publication No. WO2007/030366 to SmithKline Beecham Corp.

In particular, 5-{6-[(4-methylpiperazin-1-yl)methyl]-1H-benzimidazol-1-yl}-3-{(1R)-1-[2-(trifluoromethyl)phenyl]ethoxy}thiophene-2-carboxamide and processes for its preparation are described in PCT Publication Nos. WO2007/036061 and WO2007/030359, both to SmithKline Beecham Corp.

BRIEF SUMMARY OF THE INVENTION

As a first aspect, the present invention provides a process for preparing a compound of formula (I):

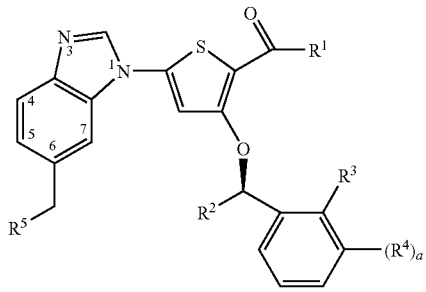

I wherein:
$R^1$ is OH, O-alkyl or $NH_2$;
$R^2$ is alkyl;
$R^3$ is F, Cl, Br, alkyl or haloalkyl,
a is 0 or 1
$R^4$ is selected from F, Cl, Br, alkyl, haloalkyl, alkenyl, cycloalkyl, cycloalkenyl, phenyl, Het, —C(O)$R^7$, —C(O)N$R^7R^8$, —O$R^7$, —O-phenyl, —O-benzyl, —O-Het, —O—$R^6$-Het; —N$R^7R^8$, —N($R^7$)C(O)$R^8$, —N($R^7$)Het, —N($R^7$)S(O)$_2R^8$, —N($R^7$)—$R^6$—S(O)$_2$$R^8$ and —CN;
  Het is selected from heterocycles and heteroaryls, wherein said heterocycle or heteroaryl may optionally be substituted with one or two substituents selected from halo, alkyl, haloalkyl, oxo, OH, O-alkyl, alkylene-OH, and alkylene-SO$_2$-alkyl;
$R^5$ is selected from —N$R^7R^8$ and N-heterocycles, wherein said N-heterocycle may optionally be substituted with one or two substituents selected from halo, alkyl, haloalkyl, oxo, OH, O-alkyl, alkylene-OH and alkylene-SO$_2$-alkyl;
$R^6$ is alkylene; and
each $R^7$ and $R^8$ are the same or different and are each independently selected from H and alkyl
or a pharmaceutically acceptable salt thereof.

The process comprises the steps of:
a) reacting a compound of formula (II):

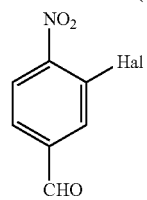

II wherein Hal is halo;
with an amine of formula H—$R^5$ to prepare a compound of formula (III) or a salt thereof:

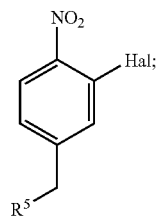

III b) cross-coupling the compound of formula (III) or a salt thereof with a compound of formula (IV) or a salt thereof:

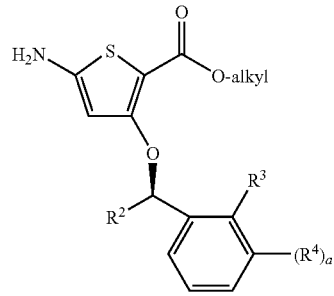

IV to prepare a compound of formula (V) or a salt thereof:

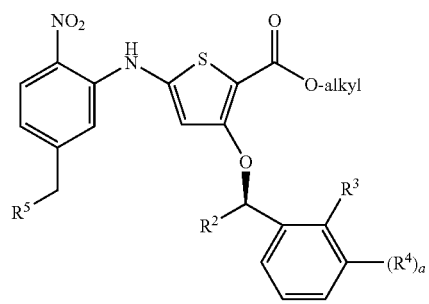

V c) reducing the compound of formula (V) or a salt thereof to prepare a compound of formula (VI) or a salt thereof:

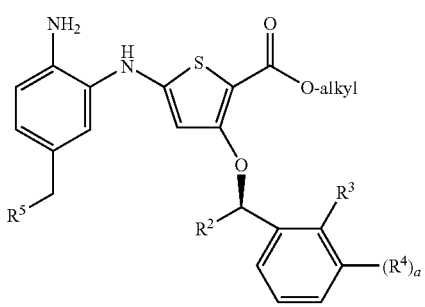

d) cyclizing the compound of formula (VI) or a salt thereof to prepare a compound of formula (I-A) or a salt thereof:

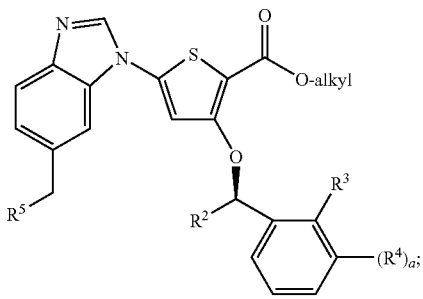

and e) optionally converting the ester compound of formula (I-A), or salt thereof, to a corresponding amide compound of formula (I-B):

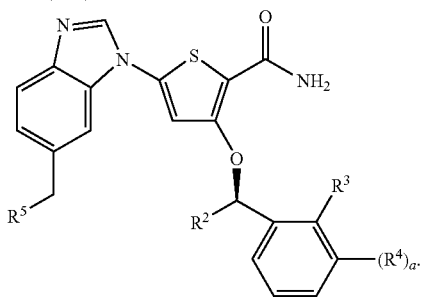

As a second aspect, the present invention provides a process for preparing a compound of formula (X):

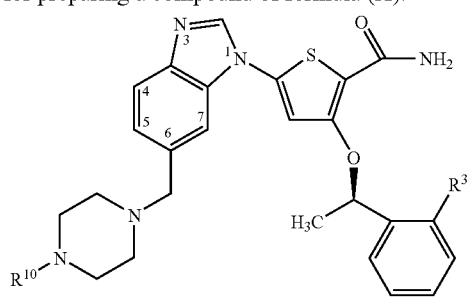

wherein:
$R^3$ is F, Cl, Br, alkyl or haloalkyl;
$R^{10}$ is H or alkyl,
or a pharmaceutically acceptable salt thereof.

The process comprises the steps of:

a) reacting 3-bromo-5-nitrobenzaldehyde:

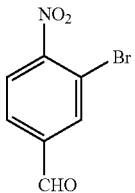

with an amine of formula:

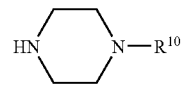

to prepare a compound of formula (III-a) or a salt thereof:

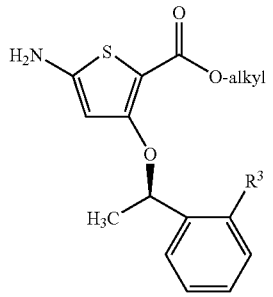

b) cross-coupling the compound of formula (III-a) or a salt thereof with a compound of formula (IV-a) or a salt thereof:

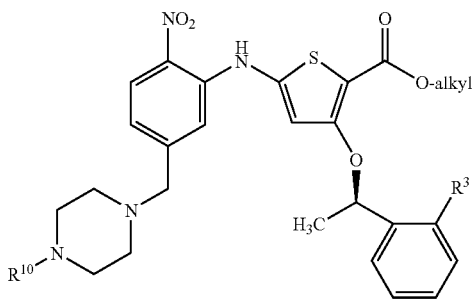

in the presence of a palladium catalyst to prepare a compound of formula (V-a) or a salt thereof:

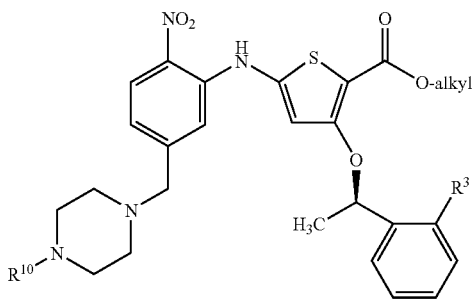

c) reducing the compound of formula (V-a) or a salt thereof to prepare a compound of formula (VI-a) or a salt thereof:

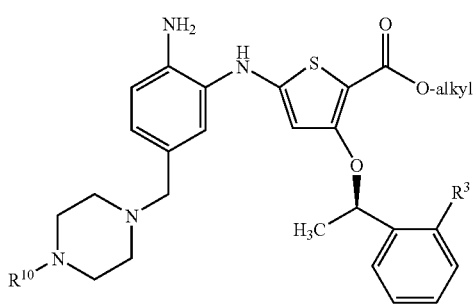

d) cyclizing the compound of formula (VI-a) or a salt thereof in the presence of an orthoester and an acid catalyst to prepare a compound of formula (IX) or a salt thereof:

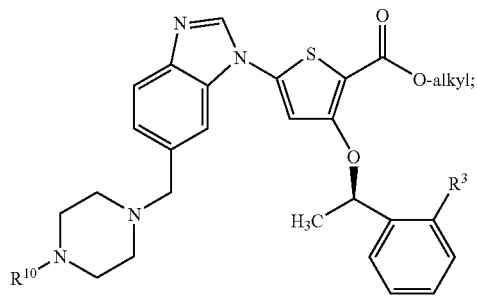

and e) converting the ester compound of formula (IX), or salt thereof to the amide compound of formula (X).

As a third aspect, the present invention provides a process for preparing 5-{6-[(4-methylpiperazin-1-yl)methyl]-1H-benzimidazol-1-yl}-3-{(1R)-1-[2-(trifluoromethyl)phenyl]ethoxy}thiophene-2-carboxamide:

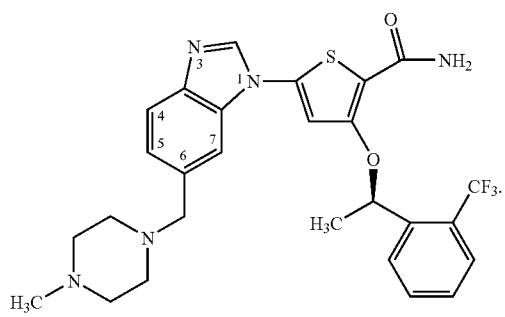

The process comprises the steps of:

a) reacting 3-bromo-5-nitrobenzaldehyde:

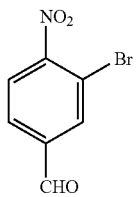

with N-methyl piperazine:

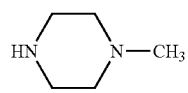

to prepare 1-[3-bromo-4-nitrophenyl)methyl]-4-methylpiperazine or a salt thereof, particularly the HCl salt thereof:

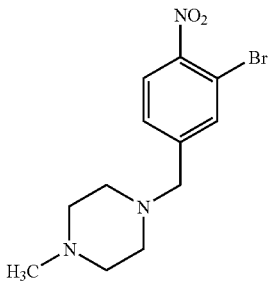

b) cross-coupling 1-[3-bromo-4-nitrophenyl)methyl]-4-methylpiperazine or a salt (e.g., HCl) thereof with methyl 5-amino-3-({(1R)-1-[2-(trifluoromethyl)phenyl]ethyl}oxy)-2-thiophenecarboxylate or a salt thereof, particularly the HCl salt thereof:

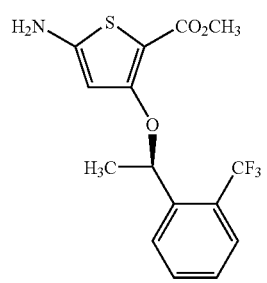

in the presence of a palladium catalyst to prepare methyl 5-({5-[(4-methyl-1-piperazinyl)methyl]-2-nitrophenyl}amino)-3-({(1R)-1-[2-(trifluoromethyl)phenyl]ethyl}oxy)-2-thiophenecarboxylate or a salt thereof, particularly the HCl salt thereof:

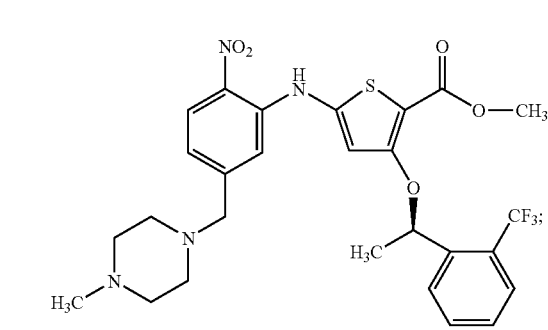

c) reducing methyl 5-({5-[(4-methyl-1-piperazinyl)methyl]-2-nitrophenyl}amino)-3-({(1R)-1-[2-(trifluoromethyl)phenyl]ethyl}oxy)-2-thiophenecarboxylate or a salt (e.g., HCl) thereof to prepare methyl 5-({2-amino-5-[(4-methyl-1-piperazinyl)methyl]phenyl}amino)-3-({(1R)-1-[2-(trifluoromethyl)phenyl]ethyl}oxy)-2-thiophenecarboxylate or a salt thereof, particularly the HCl salt thereof:

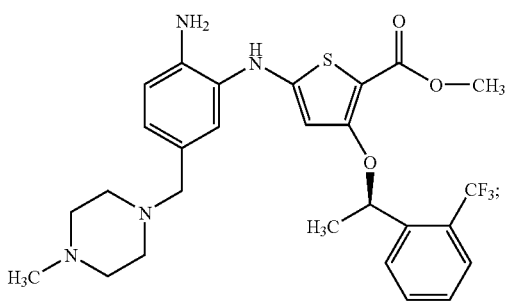

d) cyclizing methyl 5-({2-amino-5-[(4-methyl-1-piperazinyl)methyl]phenyl}amino)-3-({(1R)-1-[2-(trifluoromethyl)phenyl]ethyl}oxy)-2-thiophenecarboxylate or a salt (e.g., HCl) thereof to prepare methyl 5-{6-[(4-methyl-1-piperazinyl)methyl]-1H-benzimidazol-1-yl}-3-({(1R)-1-[2-(trifluoromethyl)phenyl]ethyl}oxy)-2-thiophenecarboxylate or a salt thereof, particularly the HCl salt thereof:

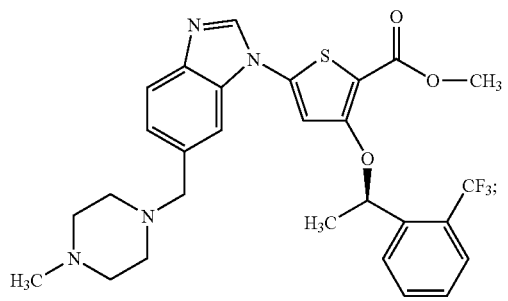

and e) reacting methyl 5-{6-[(4-methyl-1-piperazinyl)methyl]-1H-benzimidazol-1-yl}-3-({(1R)-1-[2-(trifluoromethyl)phenyl]ethyl}oxy)-2-thiophenecarboxylate or a salt (e.g., HCl) thereof with formamide and a base (e.g., sodium methoxide) to prepare 5-{6-[(4-methylpiperazin-1-yl)methyl]-1H-benzimidazol-1-yl}-3-{(1R)-1-[2-(trifluoromethyl)phenyl]ethoxy}thiophene-2-carboxamide.

These and other embodiments and aspects of the invention are described below in the Detailed Description and Examples which follow.

DETAILED DESCRIPTION OF THE PREFERRED EMBODIMENTS

The term "alkyl" as used herein refers to linear or branched hydrocarbon chains having from 1 to 8 carbon atoms (i.e., $C_{1-8}$alkyl), unless a different number of atoms is specified. Examples of "alkyl" as used herein include, but are not limited to, methyl, ethyl, n-propyl, n-butyl, n-pentyl, isobutyl, isopropyl and tert-butyl. Similarly, the term "alkylene" refers to linear or branched divalent hydrocarbon chains containing from 1 to 8 carbon atoms, unless a different number of atoms is specified. Examples of "alkylene" as used herein include, but are not limited to, methylene, ethylene, propylene, butylene and isobutylene.

As used herein, the term "alkenyl" refers to linear or branched hydrocarbon chains having from 2 to 8 carbon atoms (i.e., $C_{2-8}$alkenyl), unless a different number of atoms is specified, and at least one and up to three carbon-carbon double bonds. Examples of "alkenyl" as used herein include, but are not limited to ethenyl and propenyl.

The terms "halo" or "halogen" are synonymous and refer to fluoro, chloro, bromo and iodo unless otherwise stated.

As used herein, "haloalkyl" refers to an alkyl, as defined above, substituted by one or more halogen atoms, fluoro, chloro, bromo or iodo. Where the haloalkyl group may not have up to 8 carbon atoms, the number of carbon atoms in the group is indicated as, for example, halo$C_{1-3}$alkyl. Examples of haloalkyl as used herein include, but are not limited to fluoromethyl, difluoromethyl, trifluoromethyl, fluoroethyl, trifluoroethyl and the like.

The term "oxo" as used herein refers to the group =O attached directly to a carbon atom of a hydrocarbon ring (e.g., cyclohexyl), or a C, N or S of a heterocyclic or heteroaryl ring to result in oxides, —N-oxides, sulfones and sulfoxides.

As used herein, the term "cycloalkyl" refers to a saturated monocyclic carbocyclic ring having from 3 to 8 carbon atoms, unless a different number of atoms is specified. "Cycloalkyl" includes by way of example cyclopropyl, cyclobutyl, cyclopentyl, cyclohexyl, cycloheptyl and cyclooctyl. Where indicated, the cycloalkyl may optionally be substituted on any available carbon with one or more substituents selected from the group consisting of halo, $C_{1-3}$alkyl, halo$C_{1-3}$alkyl (e.g., perfluoroalkyl), —OH, —O—$C_{1-3}$alkyl, —NH$_2$, —NH($C_{1-3}$alkyl), —N($C_{1-3}$alkyl)$_2$ and —CN. Particular cycloalkyl groups include $C_{3-6}$cycloalkyl and substituted $C_{3-6}$cycloalkyl.

As used herein, the term "cycloalkenyl" refers to a non-aromatic monocyclic carbocyclic ring having from 3 to 8 carbon atoms (unless a different number of atoms is specified) and up to 3 carbon-carbon double bonds. "Cycloalkenyl" includes by way of example cyclobutenyl, cyclopentenyl and cyclohexenyl. "Cycloalkenyl" also includes substituted cycloalkenyl. The cycloalkenyl may optionally be substituted on any available carbon with one or more substituents selected from the group consisting of halo, $C_{1-3}$alkyl, halo $C_{1-3}$alkyl (e.g., perfluoroalkyl), —OH, —O—$C_{1-3}$alkyl, —NH$_2$, —NH($C_{1-3}$alkyl), —N($C_{1-3}$alkyl)$_2$ and —CN.

As used herein, the terms "heterocycle" and "heterocyclic" are synonymous and refer to monocyclic saturated or unsaturated non-aromatic groups having from 5 to 6 members (unless a different number of members is specified) including 1, 2 or 3 heteroatoms selected from N, O and S, unless a different number of heteroatoms is specified. In all embodiments wherein the heterocycle includes 2 or more heteroatoms, the heteroatoms may be the same or different and are independently selected from N, O and S. In all embodiments wherein the compound includes two or more heterocyclic groups, the heterocyclic groups may be the same or different and are independently selected. Examples of particular heterocyclic groups include but are not limited to tetrahydrofuran, dihydropyran, tetrahydropyran, pyran, thietane, 1,4-dioxane, 1,3-dioxane, 1,3-dioxalane, piperidine, piperazine, pyrrolidine, morpholine, thiomorpholine, thiazolidine, oxazolidine, tetrahydrothiopyran, tetrahydrothiophene and the like.

As used herein, the term "N-heterocycle" refers to monocyclic saturated or unsaturated non-aromatic groups having from 5 to 6 members (unless a different number of members is specified) including at least one N and optionally 1 or 2 additional heteroatoms selected from N, O and S, unless a different number of additional heteroatoms is specified. The N-heterocycle may be bound through the at least one N. By "additional heteroatoms" is meant 1 or 2 heteroatoms in addition to the N already specified in the N-heterocycle ring. In all embodiments wherein the heterocycle includes 1 or more additional heteroatoms, the heteroatoms may be the same or different and are independently selected from N, O and S. In all embodiments wherein the compound of formula (I) includes two or more N-heterocyclic groups, the N-heterocyclic groups may be the same or different and are independently selected. Examples of N-heterocycles include piperidine, piperazine, pyrrolidine, morpholine and thiomorpholine.

As used herein, the term "heteroaryl" refers to aromatic, monocyclic groups having from 5 to 6 members (unless a different number of members is specified) including 1, 2 or 3 heteroatoms selected from N, O and S, unless a different number of heteroatoms is specified. The N-heterocycle may be bound through the at least one N. In all embodiments wherein the heteroaryl includes 2 or more heteroatoms, the heteroatoms may be the same or different and are independently selected from N, O and S. In all embodiments wherein the compound includes two or more heteroaryl groups, the heteroaryl groups may be the same or different and are independently selected. Examples of particular heteroaryl groups include but are not limited to furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, tetrahydropyrimidine and triazine.

As used herein, the term "N-heteroaryl" refers to aromatic, monocyclic groups having from 5 to 10 members (unless a different number of members is specified) including at least one N and optionally 1 or 2 additional heteroatoms selected from N, O and S, unless a different number of heteroatoms is specified. By "additional heteroatoms" is meant 1 or 2 heteroatoms in addition to the N already present in the N-heteroaryl. In all embodiments wherein the heteroaryl includes 1 or more additional heteroatoms, the heteroatoms may be the same or different and are independently selected from N, O and S. In all embodiments wherein the compound includes two or more N-heteroaryl groups, the N-heteroaryl groups may be the same or different and are independently selected. Examples of N-heteroaryls include pyrrole, imidazole, pyrazole, thiazole, isoxazole, pyridine, pyridazine, pyrazine, pyrimidine and triazine.

As used herein, the term "members" (and variants thereof e.g., "membered") in the context of heterocyclic and heteroaryl groups refers to the total number of ring atoms, including carbon and heteroatoms N, O and/or S. Thus, an example of a 6-membered heterocyclic ring is piperidine and an example of a 6-membered heteroaryl ring is pyridine.

As used herein, the term "optionally" means that the invention includes both embodiments wherein the described condition is and is not met. Thus, an N-heterocycle optionally including 1 or 2 additional heteroatoms describes N-heterocycles including no additional heteroatoms (i.e., only one N) as well as N-heterocycles including 1 or 2 additional heteroatoms.

The present invention provides a new process for preparing compounds of formula (I):

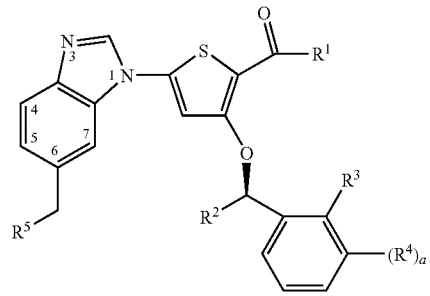

wherein:
$R^1$ is OH, O-alkyl or $NH_2$;
$R^2$ is alkyl;
$R^3$ is F, Cl, Br, alkyl or haloalkyl,
a is 0 or 1
$R^4$ is selected from F, Cl, Br, alkyl, haloalkyl, alkenyl, cycloalkyl, cycloalkenyl, phenyl, Het, —C(O)$R^7$, —C(O)N$R^7R^8$, —O$R^7$, —O-phenyl, —O-benzyl, —O-Het, —O—$R^6$-Het; —N$R^7R^8$, —N($R^7$)C(O)$R^8$, —N($R^7$)Het, —N($R^7$)S(O)$_2R^8$, —N($R^7$)—$R^6$—S(O)$_2R^8$ and —CN;
Het is selected from heterocycles and heteroaryls, wherein said heterocycle or heteroaryl may optionally be substituted with one or two substituents selected from halo, alkyl, haloalkyl, oxo, OH, O-alkyl, alkylene-OH, and alkylene-SO$_2$-alkyl;
$R^5$ is selected from —N$R^7R^8$ and N-heterocycles, wherein said N-heterocycle may optionally be substituted with one or two substituents selected from halo, alkyl, haloalkyl, oxo, OH, O-alkyl, alkylene-OH and alkylene-SO$_2$-alkyl;
$R^6$ is alkylene; and
each $R^7$ and $R^8$ are the same or different and are each independently selected from H and alkyl
and pharmaceutically acceptable salts thereof.

In one embodiment, the compounds of formula (I) are defined wherein $R^1$ is $NH_2$.

In one embodiment, $R^2$ is methyl.

In one embodiment, $R^3$ is halo or haloalkyl. In one particular embodiment, $R^3$ is haloalkyl. In one preferred embodiment, $R^3$ is trifluoromethyl.

In one embodiment, a is 0. It should be understood that when a is 0, there is no substituent $R^4$.

In one embodiment wherein a is 1, $R^4$ is selected from F, Cl, Br, alkyl, haloalkyl, cycloalkyl, phenyl, Het, —O$R^7$, —O-phenyl, —O-benzyl, —O-Het, —O—$R^6$-Het, —N$R^7R^8$, —N($R^7$)C(O)$R^8$ and —N($R^7$)Het. In one particular embodiment, $R^4$ is selected from F, Cl, Br, alkyl, haloalkyl, —O$R^7$, and —N$R^7R^8$. In another particular embodiment, $R^4$ is selected from phenyl, Het, —O-phenyl, —O-benzyl, —O-Het, —O—$R^6$-Het and —N($R^7$)Het.

In one embodiment, Het in $R^4$ (in each of the groups wherein that term is employed, e.g., Het, —O-Het, etc.) is defined wherein Het is selected from substituted and unsubstituted 5 and 6 membered N-heterocycles and N-heteroaryls, optionally having one additional heteroatom selected from N, O and S, wherein said N-heterocycle or N-heteroaryl may optionally be substituted with one or two substituents selected from alkyl, haloalkyl, oxo, OH and O-alkyl. In one embodiment, Het is selected from substituted and unsubstituted 6 membered N-heterocycles optionally having one additional heteroatom selected from N, O and S, wherein said N-heterocycle may optionally be substituted with one or two substituents selected from alkyl and haloalkyl. In one embodiment, Het is selected from substituted and unsubstituted 6 membered N-heterocycles optionally having no additional heteroatoms, wherein said N-heterocycle may optionally be substituted with one or two substituents selected from alkyl and haloalkyl.

In one embodiment, $R^5$ is —$NR^7R^8$. In another embodiment, $R^5$ is a substituted or unsubstituted 5 or 6 membered N-heterocycle, optionally having one additional heteroatom selected from N, O and S, wherein said N-heterocycle may optionally be substituted with one or two substituents selected from alkyl, haloalkyl, oxo, OH and O-alkyl. In a particular embodiment, $R^5$ is a substituted or unsubstituted 6 membered N-heterocycle, optionally having one additional heteroatom selected from N, O and S, wherein said N-heterocycle may optionally be substituted with one or two substituents selected from alkyl and haloalkyl. In one preferred embodiment, $R^5$ is piperazine substituted with alkyl.

In one embodiment, $R^6$ is $C_{1-3}$alkylene.

In one embodiment, each $R^7$ and each $R^8$ is the same or different and is independently selected from H and $C_{1-3}$alkyl.

A preferred compound which may be prepared by the process of the invention is 5-{6-[(4-Methylpiperazin-1-yl)methyl]-1H-benzimidazol-1-yl}-3-{(1R)-1-[2-(trifluoromethyl)phenyl]ethoxy}thiophene-2-carboxamide.

The pharmaceutically acceptable salts of the compounds of formula (I) include conventional salts formed from pharmaceutically acceptable inorganic or organic acids or bases as well as quaternary ammonium salts. More specific examples of suitable acid salts include hydrochloric, hydrobromic, sulfuric, phosphoric, nitric, perchloric, fumaric, acetic, propionic, succinic, glycolic, formic, lactic, maleic, tartaric, citric, palmoic, malonic, hydroxymaleic, phenylacetic, glutamic, benzoic, salicylic, fumaric, toluenesulfonic, methanesulfonic (mesylate), naphthalene-2-sulfonic, benzenesulfonic hydroxynaphthoic, hydroiodic, malic, steroic, tannic and the like.

Other acids such as oxalic, while not in themselves pharmaceutically acceptable, may be useful in the preparation of salts useful as intermediates in obtaining the compounds of the invention and their pharmaceutically acceptable salts. More specific examples of suitable basic salts include sodium, lithium, potassium, magnesium, aluminium, calcium, zinc, N,N'-dibenzylethylenediamine, chloroprocaine, choline, diethanolamine, ethylenediamine, N-methylglucamine and procaine salts.

A process according to the invention is depicted in the following scheme.

Scheme 1

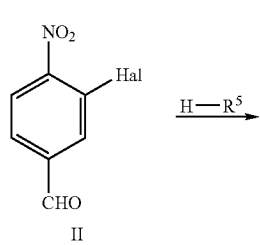

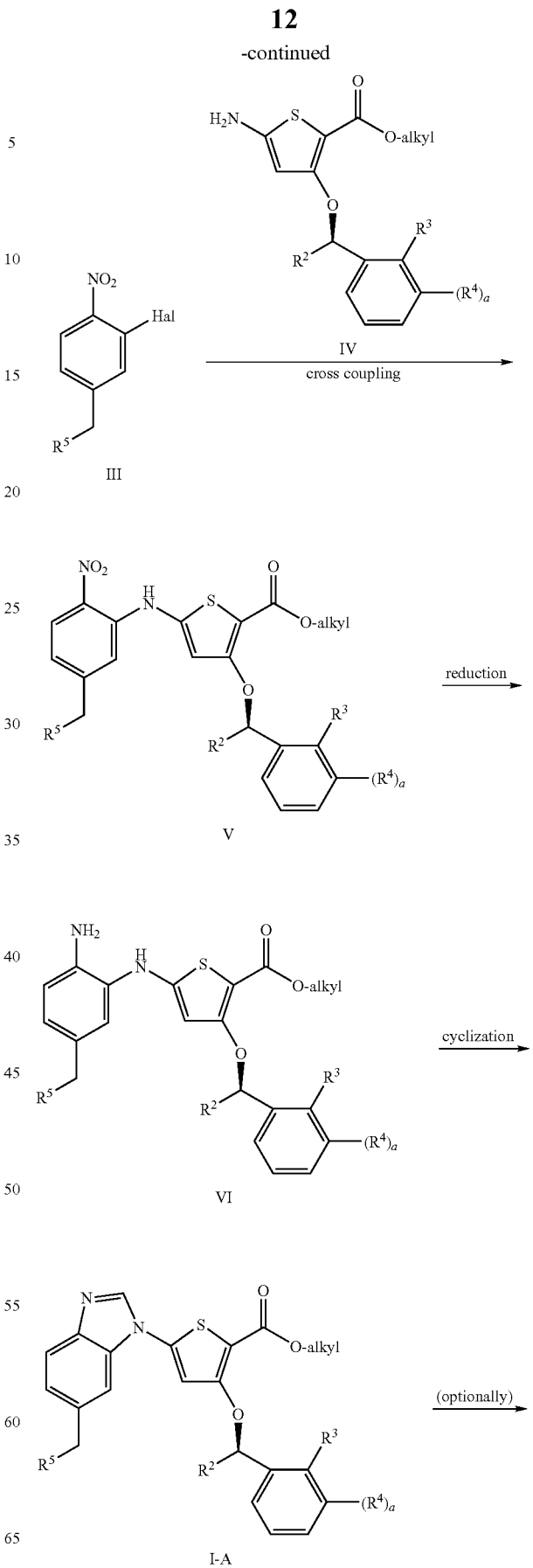

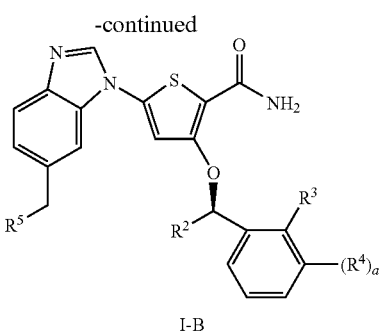

I-B

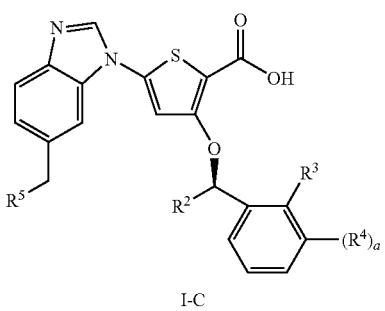

I-C wherein all variables are as defined above.

Generally, the process comprises the steps of:
a) reacting a compound of formula (II) with an amine of formula H—R$^5$ to prepare a compound of formula (III) or a salt thereof;
b) cross-coupling the compound of formula (III) or a salt thereof with a compound of formula (IV) or a salt thereof to prepare a compound of formula (V) or a salt thereof;
c) reducing a compound of formula (V) or a salt thereof to prepare a compound of formula (VI) or a salt thereof; and
d) cyclizing the compound of formula (VI) or a salt thereof to prepare a compound of formula (I-A) or a salt thereof.

Optionally, the process may further comprise the step of converting the ester compound of formula (I-A) or a salt thereof to a corresponding amide compound of formula (I-B). The process may further comprise the step of converting the ester compound of formula (I-A) or salt thereof to the acid compound of formula (I-C) or salt thereof.

More particularly, compounds of formula (III) or a salt thereof may be prepared by reacting a compound of formula (II) with an amine of formula H—R$^5$. The reaction may be carried out using reductive amination techniques. Typically, the amine and the compound of formula (II) are reacted in the presence of an acid and a reducing agent in a suitable solvent. Conveniently, the reaction may be carried out at room temperature. Suitable solvents for this reaction include but are not limited to toluene, dichloromethane, dichloroethane benzene and tetrahydrofuran. The acid may, for example, be acetic acid. Examples of suitable reducing agents for this reaction include but are not limited to sodium triacetoxyborohydride and sodium cyanoborohydride. Compounds of formula (II) are commercially available or may be prepared using conventional techniques known in the art. In one embodiment, this step of reacting the compound of formula (II) with the amine prepares the HCl salt of the compound of formula (III) through the use of HCl acid in the isolation of the product. The HCl salt may be the mono or bis HCl salt. In a particular embodiment, the HCl salt is the bis HCl, bis hydrate of the compound of formula (III).

Reaction of a compound of formula (III) or a salt thereof (e.g., HCl, particularly bis HCl bis hydrate) with a compound of formula (IV) or a salt (e.g., HCl) thereof, may be carried out using conventional cross-coupling techniques. The choice of reagents for the cross-coupling reaction will depend upon the definition of Hal in formula (III). In those embodiments wherein Hal is fluoride (F), the cross-coupling reaction is carried out in the presence of a base. Examples of suitable bases for this reaction include, but are not limited to potassium hydroxide and lithium hydroxide. Suitable solvents for this reaction include but are not limited to acetonitrile, n-butyl acetate and isopropyl acetate. The reaction may be carried out at room temperature or at elevated temperatures. In those embodiments wherein Hal is chloride (Cl), bromide (Br) or iodide (I), the reaction may be carried out by using transition metal catalyzed cross-coupling techniques conventional in the art of organic synthesis. Palladium catalyzed cross-coupling conditions are preferred. Palladium catalyzed cross-coupling conditions include but are not limited to reacting the compound of formula (III) or salt thereof with the compound of formula (IV) or salt thereof in the presence of a palladium source, a suitable ligand, and a base in a suitable inert solvent. Examples of suitable palladium sources include but are not limited to tris(dibenzylideneacetone)dipalladium(0), palladium(II) acetate and tetrakis(triphenylphosphine)palladium (0). Examples of suitable ligands include but are not limited to phosphine ligands such as 2-(di-t-butylphosphino)biphenyl and 2,2'-bis(diphenylphosphino)-1,1'-binaphthyl, 2-dicyclohexylphosphio-2',4',6'-triisopropylbiphenyl which is commercially available from Sigma-Aldrich under the name "X-Phos" (catalog no. 63,806-4) and 4,5-bis(diphenylphosphino)-9,9-dimethylxanthene, which is commercially available under the name "XANTPHOS" from Sigma-Aldrich. In one embodiment where Hal is Cl, the ligand is X-Phos. In one embodiment wherein Hal is Br, the ligand is XANTPHOS. Examples of suitable bases include but are not limited to cesium carbonate, potassium carbonate and potassium phosphate. Examples of suitable inert solvents include but are not limited to toluene, tetrahydrofuran, N,N-dimethylformamide and 1,4-dioxane. The reaction may be carried out at room temperature or elevated temperature depending upon the catalyst selected. See, Yang, B. H.; Buchwald, S. L. *Journal of Organometallic Chemistry* 1999, 576, 125-146. The reaction may be initiated at elevated temperatures and then may be cooled to room temperature.

In one embodiment, the compound of formula (III) is defined wherein Hal is F, Cl or Br. Compounds of formula (IV) and salts thereof are known in the art and may be prepared using conventional methods such as those described in PCT Publication Nos. WO2007/036061 and WO2007/030359, both to SmithKline Beecham Corp. For example, one process for preparing compounds of formula (IV) is depicted in the following Scheme.

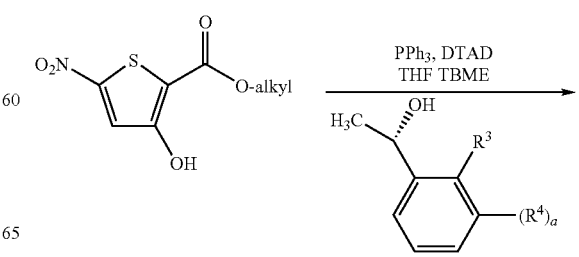

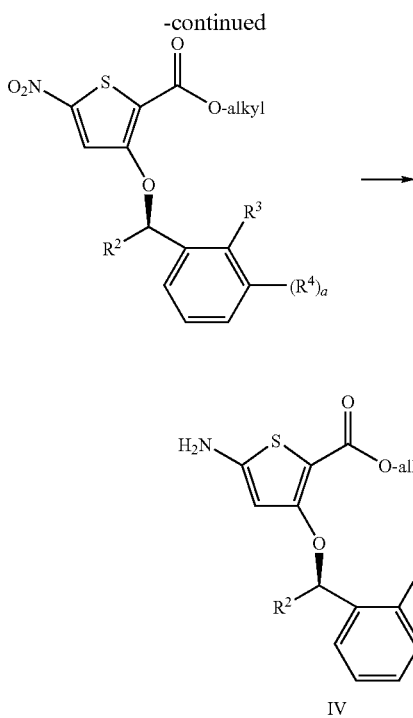

wherein:
PPh3 is triphenyl phosphine;
DTAD is di-tert-butylazodicaroxylate;
THF is tetrahydrofuran;
TBME is tert-butylmethylether
(dichloromethane may also be used as the solvent);
and all variables are as defined above.

The reaction of the compound of formula (III) or salt (e.g., HCl, particularly bis HCl bis hydrate) thereof with a compound of formula (IV) or salt (e.g., HCl) thereof prepares a compound of formula (V) or salt thereof, particularly HCl salt thereof, and more particularly bis HCl salt thereof.

The reduction of the compound of formula (V) or salt (e.g., HCl) thereof, specifically, the nitro functionality of the compound of formula (V) to the corresponding aniline compound of formula (VI) or salt thereof, particularly the HCl salt thereof, may be carried out using conventional reduction or hydrogenation techniques suitable for such compounds. In particular, the reduction may be effected using conditions such as palladium on carbon under a hydrogen atmosphere. The reaction may be carried out neat or in a solvent at elevated pressure. Suitable solvents include but are not limited to toluene, water, ethanol, methanol, ethyl acetate, THF, dioxane, and mixtures of any of the foregoing. Other suitable reduction techniques include palladium with ammonium formate, tin(II)chloride, platinum on carbon with hydrogen, platinum oxide with hydrogen, nickel with hydrogen, iron with acetic acid, aluminum with ammonium chloride, borane and sodium dithionite. The reaction may optionally be heated to between about 50 and about 120° C.

The cyclization of compounds of formula (VI) or a salt (e.g., HCl) thereof, may be carried out using a suitable cyclizing agent. Suitable cyclizing agents will be apparent to those skilled in the art of organic synthesis and include, for example triethylorthoformate or trimethylorthoformate or formic acid, optionally in the presence of an acid catalyst, such as for example, hydrochloric acid or formic acid or pyridinium p-toluenesulfonate. In one preferred embodiment, the cyclizing agent is trimethylorthoformate. Conveniently, the reaction of a compound of formula (VI) or a salt (e.g., HCl) thereof with the cyclization agent may be carried out neat, at room temperature or at elevated temperatures. The cyclization reaction prepares a compound of formula (I-A) or a salt thereof. In one embodiment, the cyclization of the compound of formula (VI) or salt thereof prepares a HCl salt of the compound of formula (I-A). In a particular embodiment, the compound of formula (I-A) is in the form of a tris HCl salt thereof.

In another embodiment, the process of preparing a compound of formula (I-A) or a salt (e.g., HCl, particularly tris HCl) thereof may be conveniently carried out by performing a one-pot reduction-cyclization procedure on a compound of formula (V) or salt (e.g., HCl) thereof using conditions such as palladium on carbon under a hydrogen atmosphere in the presence of trimethylorthoformate and excess acid catalyst. In this embodiment, trimethylorthoformate may be used as a solvent or a co-solvent with another suitable inert solvent, such as methanol.

The compound of formula (I-A) or salt (e.g., HCl, particularly tris HCl) thereof may be converted to the corresponding amide compound of formula (I-B) or acid compound of formula (I-C).

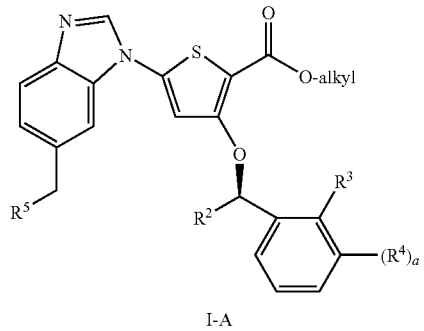

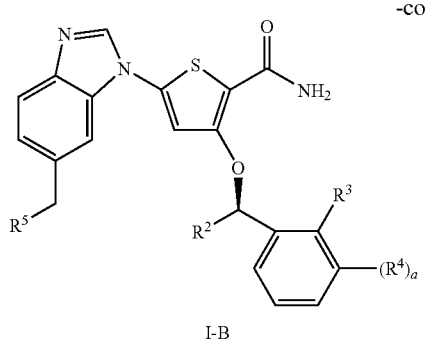

I-B

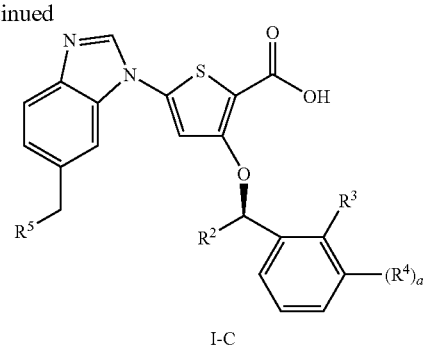

I-C wherein all variables are as defined above.

One process for preparing a compound of formula (I-B) comprises reacting the compound of formula (I-A) or salt (e.g., HCl, particularly tris HCl) with excess ammonia. Typically, the reaction is carried out by heating the reaction in a sealed vessel with an excess of ammonia at temperature of from about 50° C. to about 120° C. Suitable solvents for this reaction include but are not limited to methanol, ethanol, isopropanol, tetrahydrofuran, and dioxane.

Alternatively, the amide may be prepared by reacting the corresponding ester with formamide and a base. The reaction is typically carried out in a solvent or mixture of solvents such as tetrahydrofuran and toluene. Conveniently, the reaction may be carried out at room temperature. Preferably, the base is sodium methoxide.

A compound of formula (I-C) may be prepared by a process comprising hydrolyzing the compound of formula (I-A). The hydrolysis step may be carried out using conventional hydrolysis techniques well known to those skilled in the art.

A compound of formula (I-B) may be prepared from a compound of formula (I-C) by reacting with ammonia using conventional amide bond coupling conditions, although the foregoing method for preparing the amide of formula (I-B) from the ester for formula (I-A) is preferred. The reaction of the acid to the amide may be carried out in an inert solvent using a variety of commercially available coupling reagents. The carboxylic acid compound of formula (I-C) may optionally be converted into the corresponding acid chloride and subsequently treated with ammonia to prepare the corresponding amide. Suitable reagents for the reaction of such acid chlorides include but are not limited to oxalyl chloride, thionyl chloride, and 1-chloro-N,N,2-trimethyl-1-propenylamine. Base may be optionally added to the coupling reaction. The reaction may optionally require heating to a temperature of from about 40° C. to about 100° C. Suitable bases include but are not limited to trialkylamines, pyridine, and 4-(dimethylamino)pyridine. Examples of suitable solvents for this reaction include but are not limited to dichloromethane, chloroform, benzene, toluene, N,N-dimethylformamide and dichloroethane.

Additional transformations for converting a particular compound of formula (I) into a different compound of formula (I) are described in PCT Publication No. WO04/014899.

Within the scope of compounds of formula (I) are compounds of formula (X):

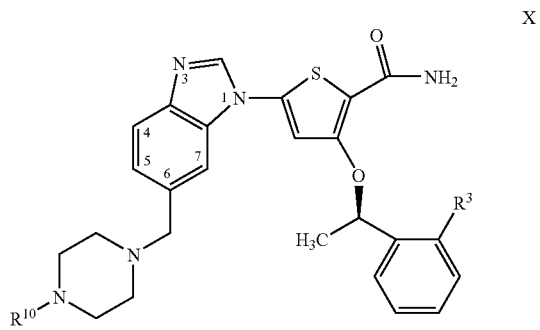

wherein:

$R^3$ is F, Cl, Br, alkyl or haloalkyl;

$R^{10}$ is H or alkyl.

In one particular embodiment, the present invention provides a process for preparing compound of formula (X) comprising the steps of:

a) reacting 3-bromo-5-nitrobenzaldehyde:

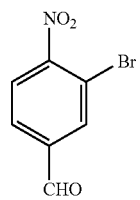

with an amine of formula:

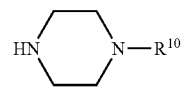

to prepare a compound of formula (III-a) or a salt thereof, particularly a HCl salt (more particularly bis HCl bis hydrate salt) thereof:

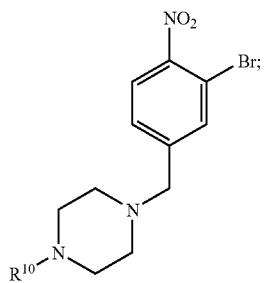

III-a b) cross-coupling the compound of formula (III-a) or salt (e.g., HCl, particularly bis HCl bis hydrate) with a compound of formula (IV-a) or salt (e.g., HCl) thereof:

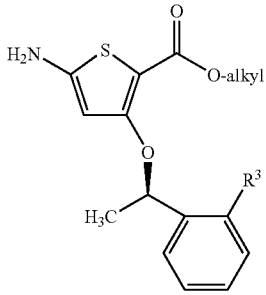

IV-a in the presence of a palladium catalyst to prepare a compound of formula (V-a) or a salt thereof, particularly HCl salt thereof, more particularly bis HCl salt thereof:

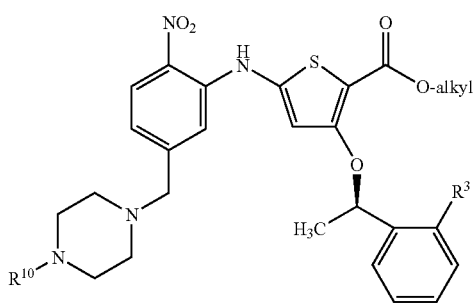

V-a c) reducing the compound of formula (V-a) or salt thereof (e.g., HCl, particularly bis HCl) to prepare a compound of formula (VI-a) or salt thereof, particularly a HCl salt thereof:

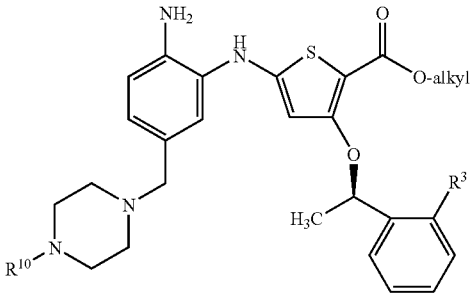

VI-a d) cyclizing the compound of formula (VI-a) or salt (e.g., HCl) thereof in the presence of an orthoester and an acid catalyst to prepare a compound of formula (IX) or a salt thereof, particularly a HCl salt thereof, more particularly a tris HCl salt thereof:

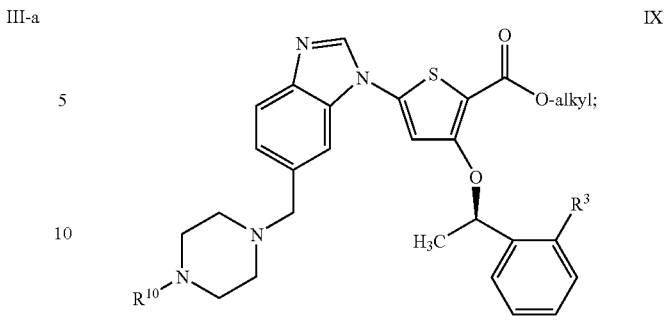

IX and e) converting the ester compound of formula (IX) or salt (e.g., HCl, particularly tris HCl salt) thereof to the corresponding amide compound of formula (X).

According to this embodiment, step a) of reacting 3-bromo-5-nitrobenzaldehyde with the indicated amine is carried out at room temperature in the presence of acetic acid and sodium triacetoxyborohydride in toluene to prepare a compound of formula (III-a) or salt (e.g., HCl, particularly bis HCl bis hydrate) thereof.

Step b) of cross-coupling the compound of formula (III-a) or salt (e.g., HCl, particularly bis HCl bis hydrate) thereof with a compound of formula (IV-a) or salt thereof is typically carried out using conventional palladium catalyzed cross-coupling conditions. Preferred cross-coupling conditions for the preparation of compounds of formula (V-a) or salts there include but are not limited to reacting the compound of formula (III-a) or salt thereof with the compound of formula (IV-a) or salt thereof in the presence of tris(dibenzylideneacetone)-dipalladium(0), XANTPHOS and cesium carbonate. The reaction may be initiated at elevated temperature of about 50° C. to about 75° C. and then cooled to room temperature. In one embodiment, the compound of formula (V-a) prepared by this method is in the form of the HCl salt, more particularly the bis HCl salt.

According to this embodiment, the reduction of the compound of formula (V-a) or salt (e.g., HCl, particularly bis HCl) thereof to the corresponding aniline compound of formula (VI-a) or salt thereof is carried out using palladium on carbon under a hydrogen atmosphere. The cyclization of the compound of formula (VI-a) or salt thereof is then carried out using trimethylorthoformate in the presence of hydrochloric acid. In one preferred embodiment, the reduction and cyclization reactions are carried out in a one-pot reaction, without isolation of the aniline of formula (VI-a) or salt thereof. In one embodiment, the compound of formula (VI-a) prepared by this method is in the form of the HCl salt.

The cyclization of a compound of formula (VI-a) or a salt (e.g., HCl) thereof, to prepare a compound of formula (IX) or salt thereof may be carried out using the methods described above for the cyclization of a compound of formula (VI) or salt thereof to prepare the ester compound of formula (I-A). According to this embodiment the cyclization agent is preferably trimethylorthoformate. The cyclization reaction prepares a compound of formula (IX) or a salt thereof. In one embodiment, the cyclization of the compound of formula (VI-a) or salt (e.g., HCl) thereof prepares a HCl salt of the compound of formula (IX). In a particular embodiment, the compound of formula (IX) is in the form of a tris HCl salt thereof.

In another embodiment, the process of preparing a compound of formula (IX) or a salt (e.g., HCl, particularly tris HCl) thereof may be conveniently carried out by performing a one-pot reduction-cyclization procedure on a compound of formula (V-a) or salt (e.g., HCl) thereof according to the method described above for the one-pot reduction cyclization procedure using a compound of formula (V).

In one embodiment, step e) of converting the ester compound of formula (IX) or salt (e.g., HCl, particularly tris HCl) thereof to the corresponding amide compound of formula (X) is carried out by reacting with formamide and a base. In one preferred embodiment, the base is sodium methoxide.

In one preferred embodiment, the present invention provides a process for preparing 5-{6-[(4-Methylpiperazin-1-yl)methyl]-1H-benzimidazol-1-yl}-3-{(1R)-1-[2-(trifluoromethyl)phenyl]ethoxy}thiophene-2-carboxamide:

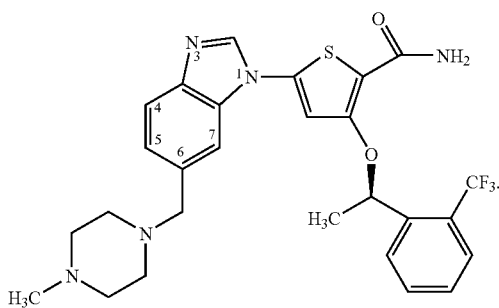

The process comprises the steps of:
a) reacting 3-bromo-5-nitrobenzaldehyde:

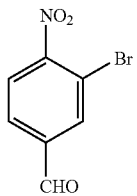

with N-methyl piperazine:

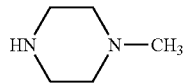

to prepare 1-[3-bromo-4-nitrophenyl)methyl]-4-methylpiperazine or a salt thereof, particularly a HCl salt (more particularly bis HCl bis hydrate salt) thereof:

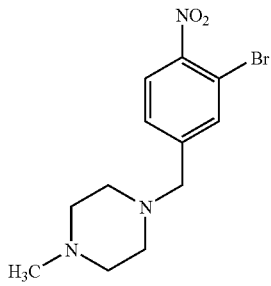

b) cross-coupling 1-[3-bromo-4-nitrophenyl)methyl]-4-methylpiperazine (or salt (e.g., HCl, particularly bis HCl) thereof) with methyl 5-amino-3-({(1R)-1-[2-(trifluoromethyl)phenyl]ethyl}oxy)-2-thiophenecarboxylate or a salt (e.g., HCl) thereof:

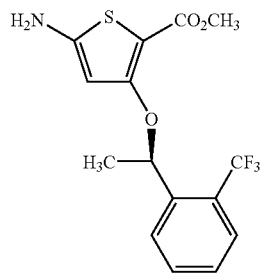

in the presence of a palladium catalyst (preferably tris(dibenzylideneacetone)-dipalladium(0)) to prepare methyl 5-({5-[(4-methyl-1-piperazinyl)methyl]-2-nitrophenyl}amino)-3-({(1R)-1-[2-(trifluoromethyl)phenyl]ethyl}oxy)-2-thiophenecarboxylate or salt thereof, particularly HCl salt thereof, more particularly bis HCl salt thereof:

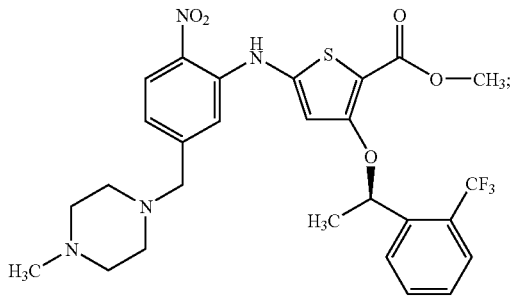

c) reducing methyl methyl 5-({5-[(4-methyl-1-piperazinyl)methyl]-2-nitrophenyl}amino)-3-({(1R)-1-[2-(trifluoromethyl)phenyl]ethyl}oxy)-2-thiophenecarboxylate (or salt (e.g., HCl, particularly bis HCl) thereof) to prepare methyl 5-({2-amino-5-[(4-methyl-1-piperazinyl)methyl]phenyl}amino)-3-({(1R)-1-[2-(trifluoromethyl)phenyl]ethyl}oxy)-2-thiophenecarboxylate or salt thereof, particularly HCl salt thereof:

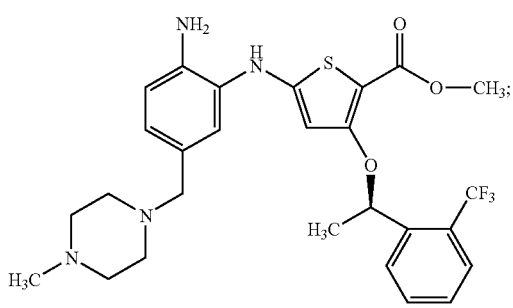

d) cyclizing methyl 5-({2-amino-5-[(4-methyl-1-piperazinyl)methyl]phenyl}amino)-3-({(1R)-1-[2-(trifluoromethyl)phenyl]ethyl}oxy)-2-thiophenecarboxylate or a salt (e.g., HCl) thereof to prepare methyl 5-{6-[(4-methyl-1- piperazinyl)methyl]-1H-benzimidazol-1-yl}-3-({(1R)-1-[2-(trifluoromethyl)phenyl]ethyl}oxy)-2-thiophenecarboxylate or salt thereof, particularly HCl salt thereof, more particularly tris HCl salt thereof:

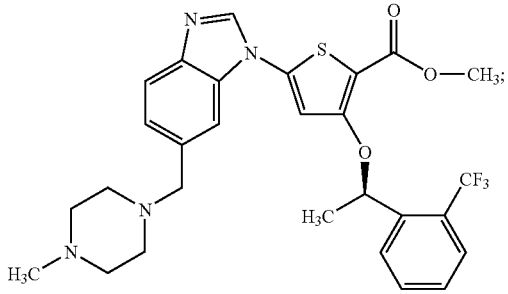

and
e) reacting methyl 5-{6-[(4-methyl-1-piperazinyl)methyl]-1H-benzimidazol-1-yl}-3-({(1R)-1-[2-(trifluoromethyl)phenyl]ethyl}oxy)-2-thiophenecarboxylate or a salt thereof (e.g., HCl, more particularly tris HCl) with formamide and a base, particularly sodium methoxide to prepare 5-{6-[(4-methylpiperazin-1-yl)methyl]-1H-benzimidazol-1-yl}-3-{(1R)-1-[2-(trifluoromethyl)phenyl]ethoxy}thiophene-2-carboxamide.

In one embodiment, steps c) of reducing and d) of cyclizing are combined as a one-pot reaction using palladium on carbon in a hydrogen atmosphere, trimethylorthoformate and excess hydrochloric acid.

The process of the present invention provides certain advantages over previously disclosed processes for preparing compounds of formula (I) for example, improved convergency and reduced number of chemical steps. The process of the present invention is suitable for the large scale production of commercial quantities of the compounds for use in the treatment of humans. The process of the present invention also enables the isolation of a number of intermediates through crystallization and/or salt-forming steps which in turn enables purification at various steps of the process.

Examples

The following examples are intended for illustration only and are not intended to limit the scope of the invention in any way, the invention being defined by the claims which follow.

The following abbreviations, as employed in the examples, have the recited meanings.

| | |
|---|---|
| g | gram(s) |
| mg | milligram(s) |
| mol | mole(s) |
| mmol | millimole(s) |
| mL | milliliter(s) |
| h | hour(s) |
| min | minute(s) |
| °C. | degrees Centigrade |
| HPLC | High Performance Liquid Chromatography |
| $Cs_2CO_3$ | cesium carbonate |
| DCM | dichloromethane |
| EtOAc | ethyl acetate |
| $H_2$ | hydrogen |
| $H_2O$ | water |
| HCl | hydrochloric acid |
| $K_2CO_3$ | potassium carbonate |
| KOH | potassium hydroxide |
| MeOH | methanol |
| $N_2$ | nitrogen |

-continued

| | |
|---|---|
| $Na_2SO_4$ | sodium sulfate |
| $NaHCO_3$ | sodium bicarbonate |
| $NEt_3$ | triethylamine |
| Pd/C | palladium on carbon |
| THF | tetrahydrofuran |

Reagents are commercially available or are prepared according to procedures in the literature.

1-[(3-Bromo-4-nitrophenyl)methyl]-4-methylpiperazine

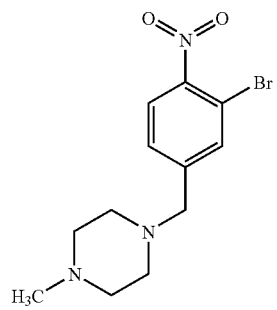

N-methyl piperazine (0.95 mL, 8.56 mmol) was added dropwise to a suspension of 3-bromo-4-nitrobenzaldehyde (0.985 g, 4.28 mmol) and acetic acid (0.29 mL, 5.14 mmol) in toluene (5.5 mL) at room temperature. The reaction mixture was stirred for 1 h at room temperature before the addition of sodium triacetoxyborohydride (1.36 g, 6.42 mmol). The reaction mixture was stirred for 2 h. Further toluene (2.1 mL) and sodium triacetoxyborohydride (0.18 g, 0.86 mmol) was added and the reaction mixture was stirred for 2 hours and then quenched by the addition of MeOH (0.99 mL). The reaction mixture was stirred for 30 min, saturated aqueous $NaHCO_3$ (6.01 mL) was then added and the reaction mixture was stirred overnight. The phases were separated and the aqueous layer was extracted with toluene (4.0 mL). The combined organic extracts were concentrated under reduced pressure and purified by flash column chromatography (EtOAc:MeOH:$NEt_3$ 9:1:0.1) to give the title compound (1.18 g, 88%) as a low melting point waxy brown solid.

$\delta_H$ (400 MHz, $CDCl_3$) 7.81 (1H, d, J 8.3, Ar H), 7.74 (1H, d, J 1.5, Ar H), 7.42 (1H, dd, J 1.7, 8.3, Ar H), 3.53 (2H, s, $NCH_2Ar$), 2.49 (8H, br s, 2×$NCH_2CH_2$), 2.31 (3H, s, $NCH_3$).

1-[(3-Bromo-4-nitrophenyl)methyl]-4-methylpiperazine dihydrochloride dihydrate

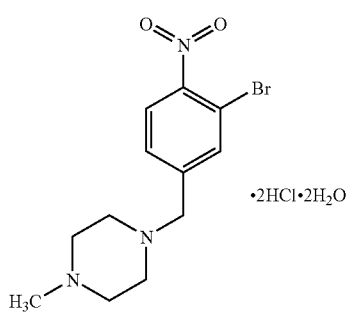

N-methyl piperazine (24.1 mL, 217 mmol) was added dropwise to a solution of 3-bromo-4-nitrobenzaldehyde (50.0 g, 217 mmol) and acetic acid (6.2 mL, 12 mmol) in THF (250 mL) at room temperature. The reaction mixture was stirred for 2 h at room temperature and then cooled to 15° C. Sodium triacetoxyborohydride (69 g, 326 mmol) was added in 6 equal portions, maintaining the internal temperature at 15±5° C. The reaction mixture was stirred for a further 2 hours, allowing warming to room temperature. The reaction was quenched by the dropwise addition of MeOH (50 mL). Aqueous sodium hydroxide (3.75 M, 250 mL) was added and the mixture was stirred at room temperature for 45 mins, then the layers separated. The aqueous phase was discarded. The organic phase was acidified with aqueous hydrochloric acid (5 M, 125 mL) and diluted with water (250 mL) and EtOAc (250 mL). The mixture was stirred vigorously for 10 minutes, then the layers were allowed to separate. The organic phase was discarded. The aqueous phase was made basic with aqueous $K_2CO_3$ (25% w/v, 300 mL) and then extracted with EtOAc (250 mL). The organic extract was heated to 45° C. Water (18 mL) was added, followed by the dropwise addition of HCl (4 M in dioxane, 109 mL) over 1 hour. The resulting slurry was aged for a further hour, cooled to room temperature, filtered, washing with EtOAc (175 mL) and dried under reduced pressure to give the title compound (75.0 g, 82% th) as a yellow crystalline solid.

$\delta_H$ (400 MHz, $D_2O$) 8.02-7.99 (2H, m, ArCH), 7.68 (1H, d, J 0.0, Ar CH), 4.47 (2H, s, $NCH_2Ar$), 3.60 (8H, br s, $N(CH_2CH_2)_2$), 2.99 (3H, s, $NCH_3$); LRMS found m/z [ES$^+$] 314 and 316, $[C_{12}H_{16}{}^{79}BrN_3O_2+H]^+$ requires 314, $[C_{12}H_{16}{}^{81}BrN_3O_2+H]^+$ requires 316.

1-[(3-fluoro-4-nitrophenyl)methyl]-4-methylpiperazine

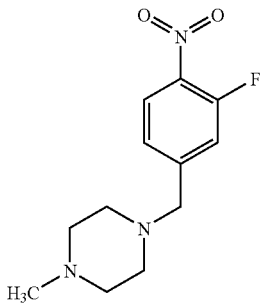

N-methyl piperazine (1.97 mL, 17.8 mmol) was added dropwise to a solution of 3-fluoro-4-nitrobenzaldehyde (1.50 g, 8.88 mmol) and acetic acid (0.20 mL, 3.54 mmol) in toluene (8.4 mL) at room temperature. The reaction mixture was stirred for 1.5 h at room temperature before the addition of further toluene (3.15 mL) and sodium triacetoxyborohydride (2.97 g, 14.0 mmol). The reaction mixture was stirred for 70 min and then further sodium triacetoxyborohydride (0.40 g, 1.9 mmol) was added. The reaction mixture was stirred for 50 min, and then quenched by the addition of MeOH (2 mL) and saturated aqueous $NaHCO_3$ (10 mL). The reaction mixture was stirred for 30 min. The phases were separated and the aqueous layer was extracted with toluene (2×20 mL, 1×10 mL). The combined organic extracts were concentrated under reduced pressure and purified by flash column chromatography (EtOAc:MeOH:$NEt_3$ 19:1:0.1) to give the title compound (1.85 g, 82%) as an orange oil.

$\delta_H$ (400 MHz, $CDCl_3$) 8.02 (1H, t, J 8.1, Ar H), 7.34 (1H, d, J 11.9, Ar H), 7.26 (1H, d, J 8.6, Ar H), 3.57 (2H, s, $NCH_2Ar$), 2.49 (8H, br s, 2×$NCH_2CH_2$), 2.31 (3H, s, $NCH_3$); LRMS found m/z [ES$^+$] 254.

1-[(3-chloro-4-nitrophenyl)methyl]-4-methylpiperazine

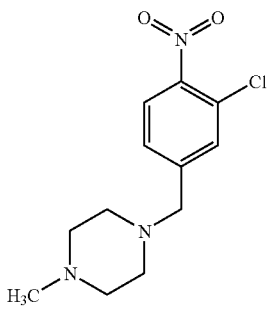

N-methyl piperazine (2.50 mL, 22.5 mmol) was added dropwise to a solution of 3-chloro-4-nitrobenzaldehyde (2.09 g, 11.3 mmol) and acetic acid (0.29 mL, 5.14 mmol) in toluene (11.7 mL) at room temperature. The reaction mixture was stirred for 1.5 h at room temperature before the addition of further toluene (4.4 mL) and sodium triacetoxyborohydride (3.58 g, 16.9 mmol). The reaction mixture was stirred at room temperature overnight and then quenched by the addition of MeOH (3 mL) and saturated aqueous $NaHCO_3$ (23 mL). The reaction mixture was stirred for 30 min. The phases were separated and the aqueous layer was extracted with toluene (2×30 mL). The combined organic extracts were concentrated under reduced pressure and purified by flash column chromatography (EtOAc:MeOH:$NEt_3$ 9:1:0.1) to give the title compound (2.17 g, 71%) as an orange oil.

$\delta_H$ (400 MHz, $CDCl_3$) 7.84 (1H, t, J 8.3, Ar H), 7.56 (1H, d, J 1.5, Ar H), 7.38 (1H, dd, J 8.3, 1.5, Ar H), 3.54 (2H, s, $NCH_2Ar$), 2.48 (8H, br s, 2×$NCH_2CH_2$), 2.30 (3H, s, $NCH_3$).

Methyl 5-({5-[(4-methyl-1-piperazinyl)methyl]-2-nitrophenyl}amino)-3-({(1R)-1-[2-(trifluoromethyl)phenyl]ethyl}oxy)-2-thiophenecarboxylate

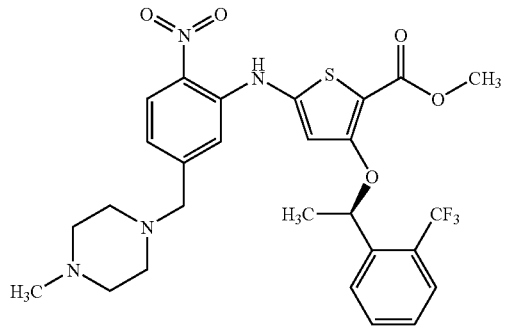

A mixture of 1-[(3-bromo-4-nitrophenyl)methyl]-4-methylpiperazine (0.675 g, 2.15 mmol), methyl 5-amino-3-({(1R)-1-[2-(trifluoromethyl)phenyl]ethyl}oxy)-2-thiophenecarboxylate (0.794 g, 2.30 mmol), $Cs_2CO_3$ (3.50 g, 10.7 mmol), XANTPHOS (0.053 g, 0.088 mmol) and tris(benzylideneacetone)dipalladium(0) (0.039 g, 0.043 mmol) in dioxane (5.4 mL) was heated to 55° C. for 1.5 h, analysed by HPLC, then cooled to room temperature. Heptane (2.4 mL), charcoal (0.27 g) and celite (0.27 g) were added. The suspension was stirred for 30 min at room temperature, and then filtered over celite, rinsing with toluene (13.5 mL×3). The filtrate was concentrated under reduced pressure and purified by flash column chromatography (DCM:MeOH: NEt₃ 9:1:0.1) to give the title compound (0.867 g, 70%) as a red amorphous solid.

$\delta_H$ (400 MHz, CDCl₃) 9.72 (1H, s, NH), 8.14 (1H, d, J 8.8, Ar H), 7.93 (1H, d, J 8.8, Ar H), 7.67-7.57 (2H, m, Ar H), 7.44-7.35 (2H, m, Ar H), 6.92 (1H, dd, J 8.8, 1.2, Ar H), 6.43 (1H, s, SC=CH), 5.73 (1H, q, J 6.4, CH₃CHO), 3.88 (3H, s, OCH₃), 3.47 and 3.41 (2×1H d, J 14.5, NCH₂Ar), 2.48 (8H, br s, 2×NCH₂CH₂), 2.30 (3H, s, NCH₃), 1.72 (3H, d, J 6.4, CH₃CHO); LRMS found m/z [ES⁻] 577.

Alternatively, methyl 5-({5-[(4-methyl-1-piperazinyl)methyl]-2-nitrophenyl}amino)-3-({(1R)-1-[2-(trifluoromethyl)phenyl]ethyl}oxy)-2-thiophenecarboxylate may be prepared by either of the following methods:

A mixture of 1-[(3-chloro-4-nitrophenyl)methyl]-4-methylpiperazine (0.313 g, 1.16 mmol), methyl 5-amino-3-({(1R)-1-[2-(trifluoromethyl)phenyl]ethyl}oxy)-2-thiophenecarboxylate (0.401 g, 1.16 mmol), K₂CO₃ (0.401 g, 2.90 mmol), X-Phos (0.0587 g, 0.12 mmol), tris(benzylideneacetone)dipalladium(0) (0.0531 g, 0.06 mmol) and tert-butanol (4.6 mL) in a sealed tube was heated at 80° C. for 18 h. The crude reaction mixture was filtered through celite, washing with toluene and then purified by flash column chromatography (EtOAc:MeOH:NEt₃) to give the title compound (0.534 g, 70%) as a red amorphous solid.

A solution of 1-[(3-fluoro-4-nitrophenyl)methyl]-4-methylpiperazine (0.733 g, 2.90 mmol) in acetonitrile (5 mL) was added dropwise to a mixture of methyl 5-amino-3-({(1R)-1-[2-(trifluoromethyl)phenyl]ethyl}oxy)-2-thiophenecarboxylate (1.00 g, 2.90 mmol) and KOH (0.325 g, 5.79 mmol) in acetonitrile (10 mL) at 0° C. The reaction mixture was allowed to warm to room temperature overnight and then heated to 40° C. for 1 h until analysis by HPLC showed complete consumption of starting materials. The reaction mixture was partitioned between EtOAc (50 mL) and H₂O (50 mL). The organic layer was washed with saturated aqueous NaHCO₃ (10 mL), concentrated under reduced pressure and then purified by flash column chromatography (DCM: MeOH 98:2 to 85:15, then EtOAC:MeOH 99:1 to 85:15) to give the title compound (0.85 g, 50%) as a red amorphous solid.

Methyl 5-({5-[(4-methyl-1-piperazinyl)methyl]-2-nitrophenyl}amino)-3-({(1R)-1-[2-(trifluoromethyl)phenyl]ethyl}oxy)-2-thiophenecarboxylate dihydrochloride

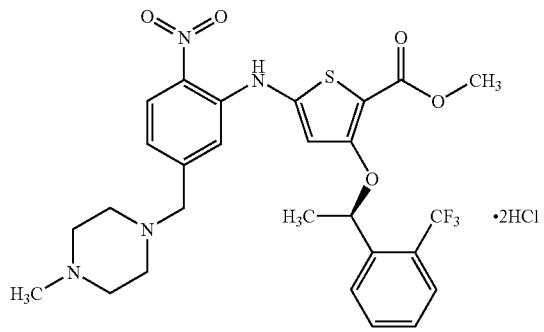

K₂CO₃ (100 g) was dissolved in water (225 mL) and the resulting solution was cooled to 25-30° C. 1-[(3-bromo-4-nitrophenyl)methyl]-4-methylpiperazine dihydrochloride (50.0 g), methyl 5-amino-3-({(1R)-1-[2-(trifluoromethyl)phenyl]ethyl}oxy)-2-thiophenecarboxylate hydrochloride (53.7 g) and 2-methyl THF (250 mL) were added and the mixture was stirred until complete dissolution had taken place. The layers were separated, retaining the organic phase. 2-Methyl tetrahydrofuran (40 mL) was added and the mixture was distilled under reduced pressure to a volume of 350-400 mL. Xantphos (2.32 g, 3 mol %) was added, followed by cesium carbonate (48.0 g) and tris(benzylideneacetone)dipalladium(0) (1.84 g, 1.5 mol %). The reaction mixture was heated to 70-75° C. until judged complete by HPLC and then cooled to 20° C. Water (250 mL) was added and the mixture stirred to dissolve the inorganics. The mixture was filtered through celite, then the phases allowed to separate. The aqueous phase was discarded. The celite was washed with MeOH (200 mL). The MeOH wash was added to the previous organic phase. The mixture was slowly added to 5 M aqueous HCl over approximately 40 minutes. The resulting crystalline slurry was stirred overnight at room temperature, then filtered, washing with MeOH (100 mL, cooled to 0° C.) and dried under reduced pressure to give the title compound (72.8 g, 87% th) as orange to red crystalline sold.

$\delta_H$ (500 MHz, CDCl₃) 13.67 (1H, s, HCl), 9.50 (1H, s, NH) 8.27 (1H, d, J 8.5, Ar CH), 7.92 (1H, d, J 8.0, Ar CH), 7.60-7.66 (2H, m, 2×Ar CH), 7.54 (1H, d, J 1.5, Ar CH), 7.41-7.47 (2H, m, Ar CH), 6.59 (1H, s, SCCH), 5.83 (1H, q, J 6.5, OCHCH₃), 4.21 (2H, 2×d, J 13.0, NCH₂Ar), 4.07 (2H, s, NCH₂CH₂), 3.90-3.97 (2H, m, NCH₂CH₂), 3.87 (3H, s, OCH₃), 3.51 (2H, d, J 13.0, NCH₂CH₂), 3.44 (2H, t, J 10.5, NCH₂CH₂), 2.89 (3H, s, NCH₃), 1.72 (d, J 6.0, OCHCH₃); LRMS found m/z [ES⁺] 579, [C₂₇H₂₉F₃N₄O₅S+H]⁺ requires 579.

Methyl 5-({2-amino-5-[(4-methyl-1-piperazinyl)methyl]phenyl}amino)-3-({(1R)-1-[2-(trifluoromethyl)phenyl]ethyl}oxy)-2-thiophenecarboxylate

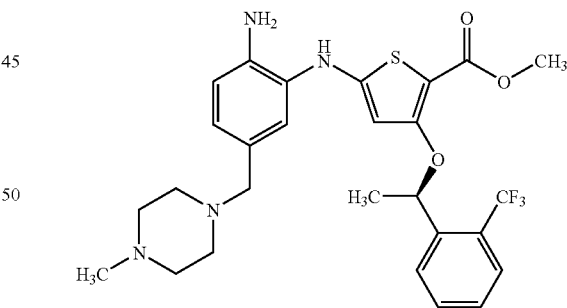

A mixture of methyl 5-({5-[(4-methyl-1-piperazinyl)methyl]-2-nitrophenyl}amino)-3-({(1R)-1-[2-(trifluoromethyl)phenyl]ethyl}oxy)-2-thiophenecarboxylate (0.24 g, 0.415 mmol), 5% Pd/C (0.144 g), HCl (1.25 M in MeOH, 0.034 mL, 0.043 mmol), trimethylorthoformate (1.66 mL, 15.2 mmol) in toluene (0.58 mL) was hydrogenated under a H₂ atmosphere at 1.1 bar pressure overnight. The vessel was purged with N₂ and the reaction mixture was analysed by HPLC to confirm presence of the title compound which was not purified, but used crude in the next step. LRMS found m/z [ES⁺] 549.

Methyl 5-{6-[(4-methyl-1-piperazinyl)methyl]-1H-benzimidazol-1-yl}-3-({(1R)-1-[2-(trifluoromethyl)phenyl]ethyl}oxy)-2-thiophenecarboxylate

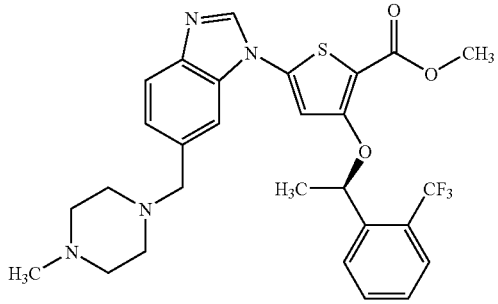

HCl (1.25 M in MeOH, 1.00 mL, 1.25 mmol) was added to a crude solution of methyl 5-({2-amino-5-[(4-methyl-1-piperazinyl)methyl]phenyl}amino)-3-({(1R)-1-[2-(trifluoromethyl)phenyl]ethyl}oxy)-2-thiophenecarboxylate from the previous step (2.5 mL). The reaction mixture was stirred for 10 min and then filtered through celite, washing with toluene (30 mL). The filtrate was concentrated under reduced pressure and partitioned between EtOAc (15 mL) and saturated aqueous $Na_2CO_3$ (15 mL) and then purified by flash column chromatography (EtOAc:MeOH:NEt$_3$ 9:1:0.1) to give the title compound (0.175 g, 75%) as a pale yellow amorphous solid.

$\delta_H$ (400 MHz, CDCl$_3$) 7.96-7.88 (2H, m, Ar H), 7.74 (1H, d, J 8.3, Ar H), 7.70-7.58 (2H, m, Ar H), 7.46-7.32 (3H, m, Ar H), 6.76 (1H, s, SC=CH), 5.83 (1H, q, J 6.1, CH$_3$CHO), 3.93 (3H, s, OCH$_3$), 3.62 and 3.58 (2×1H d, J 13.0, NCH$_2$Ar), 2.50 (8H, br s, 2×NCH$_2$CH$_2$), 2.31 (3H, s, NCH$_3$), 1.78 (3H, d, J 6.1, CH$_3$CHO); LRMS found m/z [ES$^+$] 559.

Methyl 5-{6-[(4-methyl-1-piperazinyl)methyl]-1H-benzimidazol-1-yl}-3-({(1R)-1-[2-(trifluoromethyl)phenyl]ethyl}oxy)-2-thiophenecarboxylate trihydrochloride

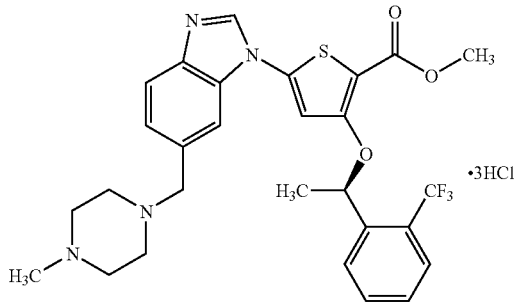

Methyl 5-({5-[(4-methyl-1-piperazinyl)methyl]-2-nitrophenyl}amino)-3-({(1R)-1-[2-(trifluoromethyl)phenyl]ethyl}oxy)-2-thiophenecarboxylate dihydrochloride (50.0 g, 76.8 mmol) was suspended in MeOH (100 mL) and trimethylorthoformate (200 mL) and stirred for half an hour. Ammonium formate (30.0 g) and 10% Pd/C (25 g, 15.4 mol %) were added and the mixture was heated to 35° C. The temperature was increased to 60° C. over 6 hours and then held at 60° C. overnight before filtering through fibreglass paper, washing with EtOAc (300 mL). The filtrate was washed with aqueous sodium hydroxide (2 M, 250 mL) and then brine (2×150 mL). A solution of HCl (4 M) was prepared by dropwise addition of acetyl chloride (16.4 mL) to MeOH (41.3 mL), cooled with an ice-bath. This solution was warmed to room temperature and then added dropwise over half an hour to the reaction mixture at 45° C. The mixture was stirred for a further half an hour at 45° C., cooled to room temperature over 1 hour and then cooled in an ice-bath for a further hour, filtered, washing with EtOAc (150 mL) and then dried under reduced pressure to give the title compound (42.7 g, 83% th) as off-white crystalline solid.

$\delta_H$ (400 MHz, D$_2$O) 8.63 (1H, s, NCHN), 7.87-7.84, 7.70-7.56 and 7.47-7.42 (7H, 4×m, Ar CH), 7.05 (1H, s, SCCH), 5.90 (1H, q, J 4.0, OCHCH$_3$), 4.49 (2H, 2×d, J 13.5, NCH$_2$), 3.90 (3H, s, OCH$_3$), 3.58 (8H, br s, N(CH$_2$CH$_2$)$_2$), 3.00 (3H, s, NCH$_3$), 1.70 (3H, d, J 5.5, CH$_3$CHO); LRMS found m/z [ES$^+$] 559, [C$_{28}$H$_{29}$F$_3$N$_4$O$_3$S+H]$^+$ requires 559.

5-{6-[(4-Methylpiperazin-1-yl)methyl]-1H-benzimidazol-1-yl}-3-{(1R)-1-[2-(trifluoromethyl)phenyl]ethoxy}thiophene-2-carboxamide

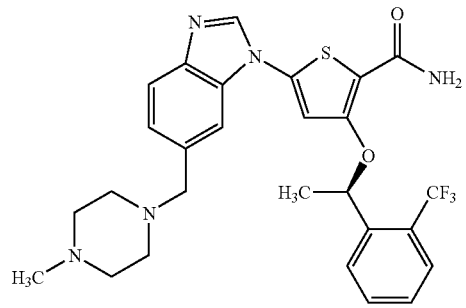

Formamide (1.08 mL, 26.5 mmol) followed by 25% w/w sodium methoxide in MeOH (1.82 mL, 7.6 mmol) are added to a solution of methyl 5-{6-[(4-methyl-1-piperazinyl)methyl]-1H-benzimidazol-1-yl}-3-({(1R)-1-[2-(trifluoromethyl)phenyl]ethyl}oxy)-2-thiophenecarboxylate (5.0 g, 8.95 mmol) in THF (50 mL) and toluene (10 mL) at room temperature. The reaction mixture is heated at ca 65° C. for about 18 h and then cooled to ca 30° C. The reaction mixture is diluted with EtOAc (25 mL) and H$_2$O (25 mL) and then the biphasic mixture is separated. The organic phase is washed sequentially with H$_2$O (25 ml), saturated aqueous Na$_2$CO$_3$ and finally H$_2$O (2×25 mL). The organic phase is then concentrated by rotary evaporation and the concentrate diluted with EtOAc (30 mL) and then heated at ca 70° C. for about 1 h. The resulting suspension is then cooled to about 20° C. and stirred at this temperature for ca 18 h. The suspension is then stirred at 0-5° C. for 2 h and the product, isolated by filtration, washed with EtOAc (5 mL) and dried under vacuum at ca 25° C. to constant weight (2.93 g, 60.2%).

$\delta_H$ (400 MHz, CDCl$_3$) $^1$H NMR (400 MHz, DMSO-d$_6$): $\delta$ 8.49 (s, 1H), 7.93 (d, 1H, J=7.87 Hz), 7.86 (br s, 1H), 7.80-7.75 (m, 2H), 7.68 (d, 1H, J=8.23 Hz), 7.56 (t, 1H, J=7.68 Hz), 7.33 (s, 1H), 7.28 (d, 1H, J=8.42 Hz), 7.15 (br s, 1H), 7.06 (s, 1H), 5.94 (q, 1H, J=6.10 Hz), 3.52 (s, 2H), 2.45-2.20 (m, 8H), 2.13 (s, 3H), 1.74 (d, 3H, J=6.22 Hz); MS (ESI): 544 [M+H]$^+$.

That which is claimed is:

1. A process for preparing a compound of formula (X):

[Structure X: benzimidazole-thiophene-carboxamide with piperazinylmethyl substituent]

wherein:
R³ is F, Cl, Br, alkyl or haloalkyl;
R¹⁰ is H or alkyl;
or a pharmaceutically acceptable salt thereof;
comprising the steps of:
a) reacting 3-bromo-5-nitrobenzaldehyde:

[Structure: 3-bromo-5-nitrobenzaldehyde]

with an amine of formula:

[Structure: HN-piperazine-N-R¹⁰]

to prepare a compound of formula (III-a) or a salt thereof:

III-a

[Structure III-a]

b) cross-coupling the compound of formula (III-a) or a salt thereof with a compound of formula (IV-a) or a salt thereof:

IV-a

[Structure IV-a: aminothiophene ester]

c) in the presence of a palladium catalyst to prepare a compound of formula (V-a) or a salt thereof:

V-a

[Structure V-a]

d) reducing the compound of formula (V-a) or a salt thereof to prepare a compound of formula (VI-a) or a salt thereof:

VI-a

[Structure VI-a]

e) cyclizing the compound of formula (VI-a) or a salt thereof in the presence of an orthoester and an acid catalyst to prepare a compound of formula (IX) or a salt thereof:

IX

[Structure IX]

and f) converting the ester compound of formula (IX), or salt thereof to the amide compound of formula (X).

2. A process for preparing 5-{6-[(4-methylpiperazin-1-yl)methyl]-1H-benzimidazol-1-yl}-3-{(1R)-1-[2-(trifluoromethyl)phenyl]ethoxy}thiophene-2-carboxamide:

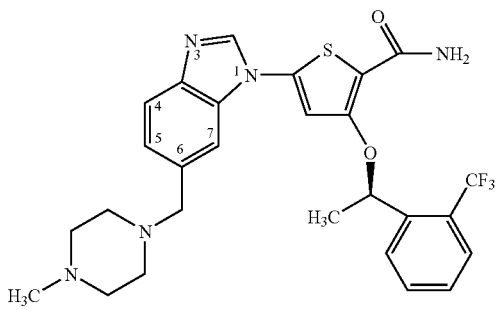

said process comprising the steps of:

a) reacting 3-bromo-5-nitrobenzaldehyde:

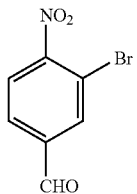

with N-methyl piperazine:

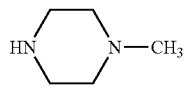

to prepare 1-[3-bromo-4-nitrophenyl)methyl]-4-methylpiperazine or a salt thereof:

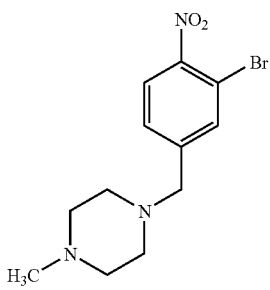

b) cross-coupling 1-[3-bromo-4-nitrophenyl)methyl]-4-methylpiperazine or a salt thereof with methyl 5-amino-3-({(1R)-1-[2-(trifluoromethyl)phenyl]ethyl}oxy)-2-thiophenecarboxylate or a salt thereof:

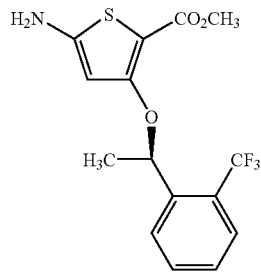

in the presence of a palladium catalyst to prepare methyl 5-({5-[(4-methyl-1-piperazinyl)methyl]-2-nitrophenyl}amino)-3-({(1R)-1-[2-(trifluoromethyl)phenyl]ethyl}oxy)-2-thiophenecarboxylate or a salt thereof:

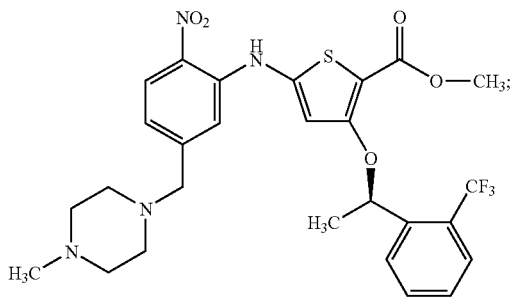

c) reducing methyl 5-({5-[(4-methyl-1-piperazinyl)methyl]-2-nitrophenyl}amino)-3-({(1R)-1-[2-(trifluoromethyl)phenyl]ethyl}oxy)-2-thiophenecarboxylate or a salt thereof to prepare methyl 5-({2-amino-5-[(4-methyl-1-piperazinyl)methyl]phenyl}amino)-3-({(1R)-1-[2-(trifluoromethyl)phenyl]ethyl}oxy)-2-thiophenecarboxylate or a salt thereof:

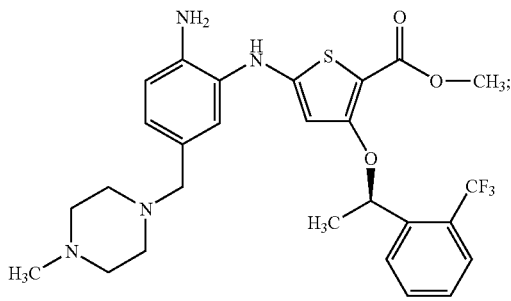

d) cyclizing methyl 5-({2-amino-5-[(4-methyl-1-piperazinyl)methyl]phenyl}amino)-3-({(1R)-1-[2-(trifluoromethyl)phenyl]ethyl}oxy)-2-thiophenecarboxylate or a salt thereof to prepare methyl 5-{6-[(4-methyl-1-piperazinyl)methyl]-1H-benzimidazol-1-yl}-3-({(1R)-1-[2-(trifluoromethyl)phenyl]ethyl}oxy)-2-thiophenecarboxylate or a salt thereof:

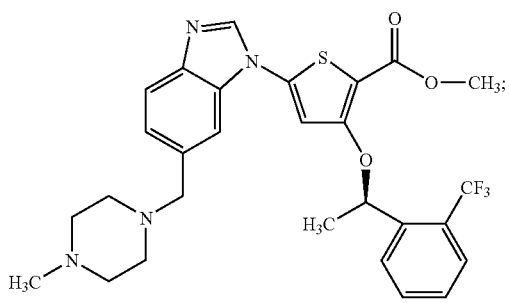

and e) reacting methyl 5-{6-[(4-methyl-1-piperazinyl)methyl]-1H-benzimidazol-1-yl}-3-({(1R)-1-[2-(trifluoromethyl)phenyl]ethyl}oxy)-2-thiophenecarboxylate or a salt thereof with formamide and a base to prepare 5-{6-[(4-methylpiperazin-1-yl)methyl]-1H-benzimidazol-1-yl}-3-{(1R)-1-[2-(trifluoromethyl)phenyl]ethoxy}thiophene-2-carboxamide.

3. The process according to claim 2, wherein said steps c) of reducing and d) of cyclizing are combined.

4. The process according to claim 2, wherein:
said step a) comprises preparing 1-[3-bromo-4-nitrophenyl)methyl]-4-methylpiperazine HCl;
said step b) comprises cross-coupling 1-[3-bromo-4-nitrophenyl)methyl]-4-methylpiperazine HCl with methyl 5-amino-3-({(1R)-1-[2-(trifluoromethyl)phenyl]ethyl}oxy)-2-thiophenecarboxylate or a salt thereof in the presence of a palladium catalyst to prepare methyl 5-({5-[(4-methyl-1-piperazinyl)methyl]-2-nitrophenyl}amino)-3-({(1R)-1-[2-(trifluoromethyl)phenyl]ethyl}oxy)-2-thiophenecarboxylate HCl;
said step c) comprises reducing methyl 5-({5-[(4-methyl-1-piperazinyl)methyl]-2-nitrophenyl}amino)-3-({(1R)-1-[2-(trifluoromethyl)phenyl]ethyl}oxy)-2-thiophenecarboxylate HCl to prepare methyl 5-({2-amino-5-[(4-methyl-1-piperazinyl)methyl]phenyl}amino)-3-({(1R)-1-[2-(trifluoromethyl)phenyl]ethyl}oxy)-2-thiophenecarboxylate HCl;
said step d) comprises cyclizing methyl 5-({2-amino-5-[(4-methyl-1-piperazinyl)methyl]phenyl}amino)-3-({(1R)-1-[2-(trifluoromethyl)phenyl]ethyl}oxy)-2-thiophenecarboxylate HCl to prepare methyl 5-{6-[(4-methyl-1-piperazinyl)methyl]-1H-benzimidazol-1-yl}-3-({(1R)-1-[2-(trifluoromethyl)phenyl]ethyl}oxy)-2-thiophenecarboxylate HCl; and
said step e) comprises reacting methyl 5-{6-[(4-methyl-1-piperazinyl)methyl]-1H-benzimidazol-1-yl}-3-({(1R)-1-[2-(trifluoromethyl)phenyl]ethyl}oxy)-2-thiophenecarboxylate HCl with formamide and sodium methoxide to prepare 5-{6-[(4-methylpiperazin-1-yl)methyl]-1H-benzimidazol-1-yl}-3-{(1R)-1-[2-(trifluoromethyl)phenyl]ethoxy}thiophene-2-carboxamide.

* * * * *